United States Patent

Naumann

[11] 4,196,304
[45] Apr. 1, 1980

[54] SEPARATION OF STEREOISOMERIC CYCLIC CARBOXYLIC ACIDS

[75] Inventor: Klaus Naumann, Cologne, Fed. Rep. of Germany

[73] Assignee: Bayer Aktiengesellschaft, Leverkusen, Fed. Rep. of Germany

[21] Appl. No.: 883,979

[22] Filed: Mar. 6, 1978

[30] Foreign Application Priority Data

Mar. 26, 1977 [DE]  Fed. Rep. of Germany ....... 2713538

[51] Int. Cl.² .............................................. C07C 51/00
[52] U.S. Cl. .................................... 562/401; 560/124
[58] Field of Search ................... 260/514 H; 562/401; 560/124

[56] References Cited

U.S. PATENT DOCUMENTS 3,538,143  11/1970  Mutsui ............................. 260/514 H
3,906,026  9/1975  Nagase ................................ 560/124

OTHER PUBLICATIONS

Otelia, J. Agr. Food Chem., pp. 767–769 (1973).

Primary Examiner—Bernard Helfin
Assistant Examiner—Michael Shippen
Attorney, Agent, or Firm—Sprung, Felfe, Horn, Lynch & Kramer

[57] ABSTRACT

A process for the separation of the stereoisomers of a stereoisomer mixture of a cyclic carboxylic acid of the formula

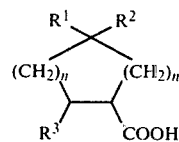

in which
 $R^1$ and $R^2$ each independently is hydrogen, halogen, $C_1$–$C_6$-alkyl or $C_2$–$C_6$-alkenyl,
 $R^3$ is alkyl, alkenyl or alkynyl having up to 6 carbon atoms and optionally substituted by halogen, or alkoxycarbonyl having up to 5 carbon atoms, or is aralkyl or aryl, or
 $R^1$ plus $R^2$, or $R^1$ plus $R^3$, together with the adjacent C atom, form a carbocyclic ring,
 $R^3$ and COOH are cis or trans to one another and the COOH group is in the exo or endo position if $R^1$ and $R^3$ together form a ring, and
 n is 0, 1 or 2, which comprises contacting a weakly alkaline, aqueous solution of the stereoisomeric mixture with a non-polar organic solvent, whereby the cis or endo isomeric free acid enters the organic solvent while the trans or exo isomer remains in the aqueous solution as a salt, and separating the aqueous solution from the organic solvent, thereby to separate the isomers. Preferred acids are cyclopropanecarboxylic acid derivatives, the aqueous solution is preferably buffered to a pH of about 7 to 9 and the organic solvent is preferably a hydrocarbon, halogenated hydrocarbon, aromatic hydrocarbon or ether.

6 Claims, No Drawings

SEPARATION OF STEREOISOMERIC CYCLIC CARBOXYLIC ACIDS

The present invention relates to a novel process for the separation of known substituted cycloaliphatic carboxylic acids into their stereoisomers.

It has already been disclosed that mixtures of stereoisomeric cis-substituted and trans-substituted cyclopropanecarboxylic acids can be separated by fractional crystallization. (Coll. Czech. Chem. Commun. 24; 2230 (1959); Pestic. Sci. 1971, 245 and Pestic. Sci. 1974, 791). However, this process is troublesome and wasteful. This process is not suitable for the preparation of relatively large amounts of pure cis and trans isomers.

The present invention now provides a process for the separation of the stereoisomers of a carboxylic acid of the general formula $$\begin{array}{c} R^1 \quad R^2 \\ (CH_2)_n \quad (CH_2)_n \\ R^3 \quad COOH \end{array} \quad (I),$$

in which
$R^1$ and $R^2$ each represents hydrogen, halogen, $C_1$-$C_6$-alkyl or $C_2$-$C_6$-alkenyl,
$R^3$ represents alkyl, alkenyl or alkynyl, which are optionally substituted by halogen and have, in each case, up to 6 C atoms, or represents aralkyl or aryl and
n represents 0, 1 or 2,
$R^1$ and $R^2$, as well as $R^1$ and $R^3$, together with the adjacent C atom, can also form a carbocyclic ring,
$R^3$ and COOH are cis or trans to one another and the COOH group is in the exo or endo position if $R^1$ and $R^3$ together form a ring, (which compounds (I), as chiral molecules, also exist in the optically active forms), in which the cis or endo isomeric free acid is removed from a weakly alkaline, aqueous solution of the trans or exo isomer, which remains in the aqueous solution as a salt, by extraction with a non-polar organic solvent.

It is surprising that the cis or endo isomer can be separated off, as the free acid, from a weakly alkaline solution by the process according to the invention.

The process according to the invention has a number of advantages. Thus, the cis or endo isomers, which are frequently present in a cis/trans or exo/endo mixture only in minor amounts, can be separated off from the large amount of the other isomers, and this can be used both for purification and for concentration purposes. Furthermore, the process according to the invention is also suitable for isolating relatively large amounts of the particular isomers and can be carried out continuously.

If, for example, 2,2-dichlorovinyl-3,3-dimethyl-cyclopropanecarboxylic acid is used as the cis/trans mixture, the process according to the invention can be represented by the following equation:

Aqueous phase before the extraction:

Aqueous phase after the extraction:

$$\begin{array}{c} Cl \\ Cl \end{array} \!\!\!\!=\!\!\!\! \triangle \!\!\!- COO^\ominus Na^\oplus \longrightarrow \begin{array}{c} Cl \\ Cl \end{array} \!\!\!\!=\!\!\!\! \triangle \!\!\!- COO^\ominus Na^\oplus +$$

cis trans organic phase:

$$\begin{array}{c} Cl \\ Cl \end{array} \!\!\!\!=\!\!\!\! \triangle \!\!\!- COO^\ominus Na^\oplus \qquad \begin{array}{c} Cl \\ Cl \end{array} \!\!\!\!=\!\!\!\! \triangle \!\!\!- COOH$$

trans cis

The compounds of the general formula (I) which are especially suitable are presented by the general formula $$\begin{array}{c} CH_3 \quad CH_3 \\ R^4 \\ R^4 \end{array} \!\!\!\!=\!\!\!\! \triangle \!\!\!- \begin{array}{c} COOH \\ H \end{array} \quad (II)$$

in which
$R^4$ represents alkyl or alkenyl with up to 4 carbon atoms, alkoxycarbonyl, F, Cl or Br.

Examples of the compounds which can be separated into stereoisomers by the process according to the invention are: 2-(2,2-difluorovinyl)-3,3-dimethyl-cyclopropanecarboxylic acid, 2-(2,2-dichlorovinyl)-3,3-dimethyl-cyclopropanecarboxylic acid, 2-(2,2-dibromovinyl)-3,3-dimethyl-cyclopropanecarboxylic acid and 2-(2-methylbuten-1-yl)-3,3-dimethylcyclopropanecarboxylic acid.

The isomer mixtures, used as the starting material, of the compounds of the general formula (I) are known (Coll. Czech. Chem. Commun. 24, 2230 (1959); DOS (German Published Specification) 2,615,159; J. Agr. Food Chem. 21, 767 (1973); British Pat. No. 1,446,304; Pestic. Sci. 1971, 245; Pestic. Sci. 1974, 537; British Patent 1,413,491; J. Chem. Soc. 1945, 285; DOS (German Published Specification) 2,432,951; J. Org. Chem. 17, 381 (1952); DOS (German Published Specification) 2,439,177; British Pat. No. 1,415,491 and Pestic. Sci. 1975, 537).

Extraction agents which can be used are non-polar solvents which are not water-miscible, such as, for example, aliphatic, optionally halogenated hydrocarbons, aromatic hydrocarbons and aliphatic ethers. Preferably, aliphatic hydrocarbons, such as petroleum ether and cyclohexane, ethers, such as diethyl ether or diisopropyl ether, or halogenated hydrocarbons, such as carbon tetrachloride, chloroform or methylene chloride, are used.

The process according to the invention can be carried out in the presence of buffer substances which maintain a constant, weakly alkaline medium. Inorganic salts of polybasic acids (including dibasic acids), such as, for example, phosphoric acid, boric acid or carbonic acid, are suitable for this. Sodium bicarbonate is preferably used. The pH range is generally between about 7 and 9, preferably between about 8 and 8.5. The separation is carried out generally at temperatures between about 0° and 100° C., preferably between about 10° and 30° C.

In general, it is not necessary to apply pressures, unless very highly volatile extraction agents, such as butane or propane or the fluorinated lower alkanes, are used.

In carrying out the process according to the invention, appropriately more that one mole of a weak inorganic base, such as sodium bicarbonate, but at least the amount of base corresponding to the proportion of trans or exo isomers previously determined analytically (for example spectroscopically or by gas chromatography), is used per mole of isomer mixture.

The subsequent procedure is to carry out the extraction, according to general laboratory practice, by shaking several times with the extraction agent, or to carry out the separation continuously with the aid of an extraction apparatus. The organic phase can then be concentrated, and the cis or endo acids can be either distilled or recrystallized for a final purification. The trans or exo isomers are obtained from the aqueous phase after acidification, filtration, separation or extraction and can be finally purified in the same manner. It is, of course, also possible to add fresh isomer mixture, as a weakly alkaline aqueous salt solution, continuously to the extraction operation, and it is also possible to carry out the operation by a counter-current distribution, in a manner such that a solution of the isomer mixture in one of the above-mentioned solvents is passed against a stream of the weakly alkaline buffer solution or of a saturated sodium bicarbonate solution, only the trans isomer being drawn off from the solution as a salt.

The stereoisomeric cyclopropanecarboxylic acids of the formula (I) obtained by the process according to the invention may be used for the preparation of highly active insecticides.

The examples which follow illustrate the process according to the invention, without indicating a limitation with regard to the range of its applicability.

EXAMPLE 1

The potassium salt of an isomer mixture of 2-(2,2-dichlorovinyl)-3,3-dimethylcyclopropanecarboxylic acid (cis/trans ratio=40/60) was dissolved in water and the resulting solution was extracted by shaking with ether. The NMR spectrum of the crystals obtained after concentrating showed that almost pure cis-(2-(2,2′-dichlorovinyl)-3,3-dimethylcyclopropanecarboxylic acid had been extracted. The substance was pure after recrystallizing once from petroleum ether at 0° C.

EXAMPLE 2

1 mole of an isomer mixture of 2-(2,2-dichlorovinyl)-3,3-dimethylcyclopropanecarboxylic acid (cis/trans ratio=40/60) was dissolved in 2.5 liters of water with the aid of 5 moles of sodium bicarbonate. A continuous, vigorous stream of fine, small bubbles of ether was allowed to bubble through this solution in an extraction apparatus. After some time, about 0.4 mole of the cis isomer was obtained by concentration of the ether layer and, after recrystallizing once from petroleum ether, was spectroscopically pure.

It will be appreciated that the instant specification and examples are set forth by way of illustration and not limitation, and that various modifications and changes may be made without departing from the spirit and scope of the present invention.

What we claim is:

1. A process for the separation of the stereoisomers of a stereoisomer mixture of a cyclic carboxylic acid of the formula

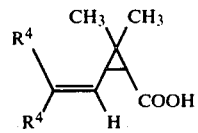

in which
R$^4$ is alkyl or alkenyl with up to 4 carbon atoms, alkoxycarbonyl with up to 5 carbon atoms, F, Cl or Br, which comprises contacting an aqueous solution of the steroisomeric mixture at a pH of about 7 to 9 with an organic solvent selected from the group consisting of an aliphatic or cycloaliphatic optionally halogenated hydrocarbon, an aromatic hydrocarbon and an aliphatic ether, whereby the cis or endo isomeric free acid enters the organic solvent while the trans or exo isomer remains in the aqueous solution as a salt, and separating the aqueous solution from the organic solvent, thereby to separate the isomers.

2. A process according to claim 1, in which the cyclic carboxylic acid is a member selected from the group consisting of 2-(2,2-difluorovinyl)-3,3-dimethyl-cyclopropanecarboxylic acid, 2-(2,2-dichlorovinyl)-3,3-dimethyl-cyclopropanecarboxylic acid, 2-(2,2-dibromovinyl)-3,3-dimethyl-cyclopropanecarboxylic acid and 2-(2-methylbuten-1-yl)-3,3-dimethyl-cyclopropanecarboxylic acid.

3. A process according to claim 1, in which the organic solvent is petroleum ether, cyclohexane, diethyl ether, diisopropyl ether, carbon tetrachloride, chloroform or methylene chloride.

4. A process according to claim 1, in which the separation is effected in the presence of a buffering agent comprising an inorganic salt of a polybasic acid.

5. A process according to claim 4, in which the buffering agent is sodium bicarbonate.

6. A process according to claim 2, in which the aqueous solution contains sodium bicarbonate as a buffering agent and has a pH between about 8 and 8.5, the organic solvent is petroleum ether, cyclohexane, diethyl ether, diisopropyl ether, carbon tetrachloride, chloroform or methylene chloride, the contact is effected at a temperature from about 0° to 100° C., and the cis/trans ratio of the starting cyclic carboxylic acid is about 40/60.

* * * * *